(12) United States Patent
Giroud et al.

(10) Patent No.: US 7,335,348 B2
(45) Date of Patent: Feb. 26, 2008

(54) HAIRSTYLING COMPOSITION WHICH MAKES POSSIBLE REMODELLING OF THE HAIRSTYLE AND PROCESS FOR REMODELLING THE HAIRSTYLE USING SUCH A COMPOSITION

(75) Inventors: Franck Giroud, Clichy (FR); Henri Samain, Bièvres (FR)

(73) Assignee: L'Oreal, Paris (FR)

( * ) Notice: Subject to any disclaimer, the term of this patent is extended or adjusted under 35 U.S.C. 154(b) by 696 days.

(21) Appl. No.: 10/330,026

(22) Filed: Dec. 27, 2002

(65) Prior Publication Data

US 2003/0143180 A1 Jul. 31, 2003

Related U.S. Application Data

(63) Continuation of application No. 09/907,459, filed on Jul. 18, 2001, now abandoned.

(30) Foreign Application Priority Data

Jul. 18, 2000 (FR) .................................. 00 09406

(51) Int. Cl.
*A61K 7/06* (2006.01)
*A61K 7/11* (2006.01)
(52) U.S. Cl. ............... 424/70.1; 424/70.11; 424/70.16; 424/401
(58) Field of Classification Search ............... 424/401, 424/70.1, 70.2, 70.11, 70.16
See application file for complete search history.

(56) References Cited

U.S. PATENT DOCUMENTS

| 2,047,398 A | 7/1936 | Voss et al. .................. 260/2 |
| 2,102,113 A | 12/1937 | Djordjevitch ................ 261/75 |
| 2,723,248 A | 11/1955 | Wright ....................... 260/45.5 |
| 3,589,578 A | 6/1971 | Kamphausen ................ 226/40 |
| 3,836,537 A | 9/1974 | Boerwinkle et al. ........ 260/29.6 |
| 4,031,307 A | 6/1977 | DeMartino et al. ......... 536/114 |
| 4,128,631 A | 12/1978 | Lundmark et al. ............. 424/70 |
| 4,131,576 A | 12/1978 | Iovine et al. ........ 260/17.4 GC |
| 4,172,122 A | 10/1979 | Kubik et al. .................. 424/59 |
| 4,693,935 A | 9/1987 | Mazurek ...................... 428/352 |
| 4,728,571 A | 3/1988 | Clemens et al. ............. 428/352 |
| 4,972,037 A | 11/1990 | Garbe et al. ................. 526/245 |
| 5,009,880 A * | 4/1991 | Grollier et al. ............... 424/47 |
| 5,593,680 A | 1/1997 | Bara et al. ................... 424/401 |
| 6,139,849 A * | 10/2000 | Lesaulnier et al. ......... 424/401 |

FOREIGN PATENT DOCUMENTS

| DE | 2 330 956 | 1/1974 |
| EP | 0 080 976 | 6/1983 |
| EP | 0 412 704 | 2/1991 |
| EP | 0 412 707 | 2/1991 |
| EP | 0 582 152 | 2/1994 |
| EP | 0 619 111 | 10/1994 |
| EP | 0 637 600 | 2/1995 |
| EP | 0 648 485 | 4/1995 |
| EP | 0 751 162 | 1/1997 |
| EP | 0 761 199 | 3/1997 |
| EP | 0 919 219 | 6/1999 |
| EP | 1 004 288 | 5/2000 |
| FR | 1222944 | 4/1959 |
| FR | 1400366 | 5/1963 |
| FR | 1564110 | 3/1968 |
| FR | 1580545 | 9/1969 |
| FR | 2077143 | 10/1971 |
| FR | 2198719 | 4/1974 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 743 297 | 7/1997 |
| FR | 2 749 568 | 12/1997 |
| GB | 839805 | 6/1960 |
| LU | 75370 | 2/1978 |
| LU | 75371 | 2/1978 |
| WO | 93/23009 | 11/1993 |
| WO | 93/23446 | 11/1993 |
| WO | 94/03510 | 2/1994 |
| WO | 95/00578 | 1/1995 |
| WO | 98/25710 | 6/1998 |
| WO | WO 98/25710 * | 6/1998 |

* cited by examiner

*Primary Examiner*—Johann R. Richter
*Assistant Examiner*—Konata M. George
(74) *Attorney, Agent, or Firm*—Jacobson Holman PLLC

(57) ABSTRACT

The invention relates to a styling composition comprising, in a physiologically acceptable liquid medium, the combination of at least one film-forming fixing polymer and of at least one crystalline hot-melt polymer which is soluble in the said medium and which has a crystalline melting temperature, measured by differential scanning calorimetry, of between 30° C. and 80° C., and to a process for the thermal remodelling of the hair using this composition.

13 Claims, No Drawings

HAIRSTYLING COMPOSITION WHICH MAKES POSSIBLE REMODELLING OF THE HAIRSTYLE AND PROCESS FOR REMODELLING THE HAIRSTYLE USING SUCH A COMPOSITION

This is a continuation of application Ser. No. 09/907,459 filed Jul. 18. 2001 now abandoned.

The present invention relates to a hairstyling composition which makes possible remodelling of the hairstyle and to a process for remodelling the hairstyle using such a composition.

There are numerous styling products in the form of lacquers, sprays, gels or lotions. These products are solutions or dispersions of polymers which, after evaporation of the solvent phase, provide for the fixing and the form retention of the hairstyle by virtue of the formation of polymer films surrounding each hair in the manner of a sheath by virtue of the establishment of physical bonds between the hairs.

This type of fixing of the hairstyle is definitive, so that any significant modification to the form of the hairstyle leads to irreversible breaking of the junction points and consequently has a detrimental effect on the form retention of the hairstyle. Conventional styling products thus do not allow remodelling of the hairstyle without introduction of additional styling product.

The Applicant Company has noticed that it is possible to overcome this disadvantage of known styling products by combining, with the fixing polymers commonly used in hairstyling, a crystalline hot-melt polymer with a low crystalline melting point.

The addition of this hot-melt polymer to the conventional fixing products is reflected by "plasticization" of the polymer film surrounding the hairs at temperatures close to or greater than the crystalline melting temperature of the said crystalline hot-melt polymer.

The hairs, thus surrounded by a sheath which becomes plastic by heating, can again be styled and shaped. Simple cooling of the hairstyle to a temperature below the crystalline melting temperature of the hot-melt polymer will be reflected by resolidification of the fixing composition, by the establishment of new physical junction points between the hairs and thus by a form retention equivalent to that obtained during the first spraying of the fixing product.

The "thermoplasticity" of the composition at relatively low temperatures thus makes possible remodelling of the hairstyle without the introduction of additional styling material.

A subject-matter of the present invention is consequently a styling composition comprising, in a physiologically acceptable liquid medium, the combination of at least one film-forming fixing polymer and of at least one crystalline hot-melt polymer which is soluble in the said medium and which has a crystalline melting temperature, measured by differential scanning calorimetry, of between 30° C. and 80° C.

An additional subject-matter of the present invention is a process for modelling or remodelling the hair which consists in applying the above styling composition to dry or wet hair, in giving the hair the desired shape by heating the hair by means of an appropriate heat source to a temperature close to or greater than the crystalline melting temperature of the crystalline hot-melt polymer present in the styling composition, and in allowing the hair to cool to a temperature below the said crystalline melting temperature of the said crystalline hot-melt polymer, it being possible for these latter two stages to be repeated many times without the introduction of additional styling composition.

Any film-forming fixing polymer known as such in the field of hair treatments, and, of course, also mixtures comprising several of these polymers, can be used for the present invention. Conventionally, cationic, anionic, amphoteric and nonionic fixing polymers are distinguished.

The cationic fixing polymers which can be used according to the present invention are preferably chosen from polymers comprising primary, secondary, tertiary and/or quaternary amine groups forming part of the polymer chain or directly bonded to the latter and having a molecular weight of between 500 and approximately 5 000 000 and preferably between 1 000 and 3 000 000.

Mention may more particularly be made, among these polymers, of the following cationic polymers:

(1) homopolymers or copolymers derived from acrylic or methacrylic esters or amides comprising at least one of the following units:

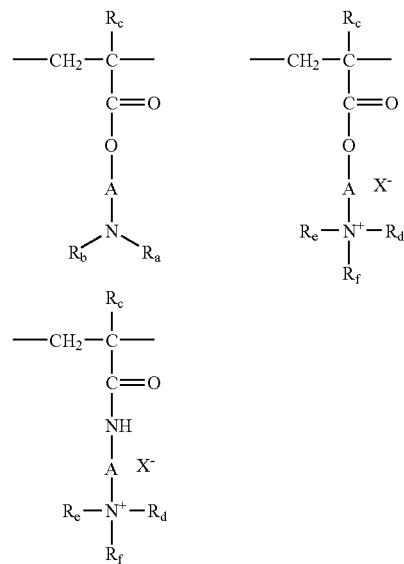

in which:

$R_a$ and $R_b$ each represent a hydrogen atom or a $C_{1-6}$ alkyl group, $R_c$ denotes a hydrogen atom or a $CH_3$ radical, $R_d$, $R_e$ and $R_f$, which are identical or different, each represent a $C_{1-18}$ alkyl group or a benzyl radical, A is a linear or branched $C_{1-6}$ alkyl group or a $C_{1-4}$ hydroxyalkyl group, and $X^-$ denotes a methyl sulphate halide or anion, such as a chloride or bromide ion.

The copolymers of the family (1) additionally comprise one or more units deriving from comonomers which can be chosen from the family of acrylamides, methacrylamides, diacetone acrylamides, acrylamides and methacrylamides substituted on the nitrogen by lower alkyl groups, acrylic or methacrylic acids or their esters, vinyllactams, such as vinylpyrrolidone or vinyl-caprolactam, and vinyl esters.

Thus, mention may be made, among the copolymers of the family (1), of:

copolymers of acrylamide and of dimethylaminoethyl methacrylate quaternized with dimethyl sulphate or with a dimethyl halide, such as that sold under the name Hercofloc® by Hercules, copolymers of acrylamide and of methacryloyloxy-ethyl-trimethylammonium chloride which is disclosed, for example, in Patent Application EP-A-080 976 and are sold under the name Bina Quat® P 100 by Ciba-Geigy, the copolymer of acrylamide and of methacryloyloxy-ethyltrimethylammonium methyl sulphate sold under the name Reten® by Hercules, optionally quaternized vinylpyrrolidone/dialkyl-aminoalkyl acrylate or methacrylate copolymers, such as the products sold under the name Gafquat® by ISP, such as, for example, Gafquat® 734 or Gafquat® 755, or else the products named Copolymer® 845, 958 and 937. These polymers are disclosed in detail in French Patents 2 077 143 and 2 393 573, dimethylaminoethyl methacrylate/vinylcaprolactam/vinylpyrrolidone terpolymers, such as the product sold under the name Gaffix VC 713 by ISP, and the quaternized dimethylaminopropyl methacrylamide/vinylpyrrolidone copolymer, such as the product sold under the name Gafquat® HS 100 by ISP.

(2) quaternized polysaccharides, disclosed more particularly in U.S. Pat. Nos. 3,589,578 and 4,031,307, such as guar gums comprising cationic trialkylammonium groups.

Such products are sold in particular under the trade names Jaguar® C13 S, Jaguar® C15 and Jaguar® C17 by Meyhall.

(3) quaternary copolymers of vinylpyrrolidone and of vinylimidazole, such as the products sold by BASF under the name Luviquat® TFC.

(4) chitosans or their salts, in particular chitosan acetate, lactate, glutamate, gluconate or pyrrolidone-carboxylate.

Mention may be made of the chitosan having a degree of deacetylation of 90.5% by weight sold under the name Kytan Brut Standard® by Aber Technologies or the chitosan pyrrolidone-carboxylate sold under the name Kytamer® PC by Amerchol.

(5) cationic cellulose derivatives, such as copolymers of cellulose or cellulose derivatives grafted with a water-soluble monomer comprising a quaternary ammonium group, which are disclosed in particular in U.S. Pat. No. 4,131,576, such as hydroxyalkylcelluloses, for example hydroxy-methyl-, hydroxyethyl- or hydroxypropylcelluloses, grafted in particular with a methacryloyloxyethyltrimethylammonium, methacrylamidopropyltrimethylammonium or dimethyldiallylammonium salt.

The commercial products corresponding to this definition are more particularly the products sold under the name Celquat® L 200 and Celquat® H 100 by National Starch.

The anionic fixing polymers generally used are polymers comprising groups derived from a carboxylic, sulphonic or phosphoric acid and have a weight-average molecular weight of approximately 500 to 5 000 000.

The carboxylic acid groups are contributed by unsaturated monomers comprising one or two carboxylic acid functional groups, such as those corresponding to the formula:

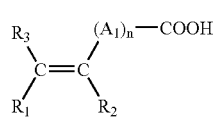

(I)

in which n is an integer from 0 to 10, $A_1$ denotes a methylene group, optionally connected to the carbon atom of the unsaturated group or of the neighbouring methylene group, when n is greater than 1, via a heteroatom, such as oxygen or sulphur, $R_3$ denotes a hydrogen atom or a phenyl or benzyl group, $R_1$ denotes a hydrogen atom or a lower alkyl or carboxyl group, and $R_2$ denotes a hydrogen atom, a lower alkyl group or a —$CH_2$—COOH, phenyl or benzyl group.

In the abovementioned formula, a lower alkyl radical preferably denotes a group having from 1 to 4 carbon atoms and in particular a methyl or ethyl group.

The preferred carboxylated anionic fixing polymers according to the invention are:

A) homo- or copolymers of acrylic or methacrylic acid or their salts and in particular the products sold under the names Versicol® E or K by Allied Colloid and under the name Ultrahold® by BASF; copolymers of acrylic acid and of acrylamide sold in the sodium salt form under the names Reten® 421, 423 or 425 by Hercules; or sodium salts of polyhydroxycarboxylic acids.

B) copolymers of acrylic acid or of methacrylic acid and of a monoethylenic monomer, such as ethylene, styrene, vinyl esters, or esters of acrylic or methacrylic acid.

These copolymers can be grafted onto a polyalkylene glycol, such as polyethylene glycol, and are optionally crosslinked.

Such polymers are disclosed in particular in French Patent FR 1 222 944 and in German Patent Application DE 2 330 956. Mention may in particular be made of the copolymers comprising, in their chain, an optionally-alkylated and/or hydroxyalkylated acrylamide unit, such as those disclosed in Luxembourgian Patent Applications LU 75370 and LU 75371 or provided under the name QuadramerÒ by American Cyanamid.

Mention may also be made of copolymers of acrylic acid and of $C_1$-$C_4$ alkyl methacrylate and terpolymers of vinylpyrrolidone, of (meth)acrylic acid and of $C_1$-$C_{20}$ alkyl (meth)acrylate, for example lauryl (meth)acrylate (Acrylidone® LM from ISP), tert-butyl (meth)acrylate (Luviflex® VBM 70, sold by BASF) or methyl (meth)acrylate (Stepanhold® Extra, sold by Stepan), and methacrylic acid/ethyl acrylate/tert-butyl acrylate terpolymers, such as the product sold under the name Luvimer® 100 P by BASF.

C) copolymers derived from crotonic acid, such as those comprising, in their chain, vinyl acetate or propionate units and optionally other monomers, such as; allyl, methallyl or vinyl esters of a linear or branched saturated carboxylic acid with a long hydrocarbonaceous chain comprising at least 5 carbon atoms, it being possible for these polymers optionally to be grafted and crosslinked, or vinyl, allyl or methallyl esters of an a- or β-cyclic acid.

Such polymers are disclosed, inter alia, in French Patents FR 1 222 944, FR 1 580 545, FR 2 265 782, FR 2 265 781, FR 1 564 110 and FR 2 439 798.

Mention may be made, as examples of commercial products coming within this category, of the resins 28-29-30, 26-13-14 and 28-13-10 sold by National Starch.

D) copolymers derived from monounsaturated $C_4$-$C_8$ carboxylic acids or anhydrides chosen from:

copolymers comprising
(i) one or more maleic, fumaric or itaconic acids or anhydrides and
(ii) at least one monomer chosen from vinyl esters, vinyl ethers, vinyl halides, phenylvinyl derivatives, or acrylic acid and its esters, the anhydride functional groups of these copolymers being optionally monoesterified or monoamidated.

Such polymers are disclosed in particular in U.S. Pat. Nos. 2,047,398, 2,723,248, 2,102,113 and GB 839 805 and in particular those sold under the names Gantrez AN or ES, or Avantage® CP by ISP.

copolymers comprising (i) one or more maleic, citraconic or itaconic anhydrides and (ii) one or more monomers chosen from allyl or methallyl esters optionally comprising one or more acrylamide, methacrylamide, a-olefin, acrylic or methacrylic ester, acrylic or methacrylic acid, or vinylpyrrolidone groups in their chain, the anhydride functional groups of these copolymers being optionally monoesterified or monoamidated.

These polymers are, for example, disclosed in French Patents FR 2 350 384 and FR 2 357 241 of the Applicant Company.

E) polyacrylamides comprising carboxylate groups.

The anionic groups of the anionic fixing polymers of the present invention can also be sulphonic acid groups contributed by vinylsulphonic, styrenesulphonic, naphthalenesulphonic or acrylamidoalkylsulphonic units.

These polymers comprising sulphonic acid groups are chosen in particular from:

salts of poly(vinylsulphonic acid) having a weight-average molecular weight of between approximately 1 000 and 100 000, and copolymers of vinylsulphonic acid and of an unsaturated comonomer, such as acrylic acid, methacrylic acid, the esters of these acids, acrylamide, acrylamide derivatives, vinyl ethers and vinylpyrrolidone;

salts of poly(styrenesulphonic acid). Mention may be made, as an example, of two sodium salts having a weight-average molecular weight of approximately 500 000 and of approximately 100 000 sold respectively under the names FlexanO 500 and FlexanO 130 by National Starch. These compounds are disclosed in Patent FR 2 198 719;

salts of poly(acrylamidosulphonic acid), such as those mentioned in U.S. Pat. No. 4,128,631 and more particularly the poly(acrylamidoethylpropanesulphonic acid) sold under the name Cosmedia PolymerO HSP 1180 by Henkel.

According to the invention, the anionic fixing polymers are preferably chosen from acrylic acid copolymers, such as the acrylic acid/ethyl acrylate/N-tert-butylacrylamide terpolymers sold in particular under the name Ultrahold Strong® by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold in particular under the name Résine 28-29-30 by National Starch, copolymers derived from maleic, fumaric or itaconic acid or anhydride comprising, as comonomers, vinyl esters, vinyl ethers, vinyl halides, phenylvinyl derivatives, acrylic acid and the esters of acrylic acid, such as the methyl vinyl ether/monoesterified maleic anhydride copolymers sold, for example, under the name GantrezÒ by ISP, the copolymers of methacrylic acid and of methyl methacrylate sold under the name Eudragit® L by Rohm Pharma, the methacrylic acid/methyl methacrylate/$C_{1-4}$ alkyl acrylate/acrylic acid or $C_{1-4}$ hydroxyalkyl methacrylate copolymers sold under the name Amerhold® DR 25 by Amerchol or under the name Acudyne® 255 by Rohm & Haas, the copolymers of methacrylic acid and of ethyl acrylate sold under the name Luvimer® MAEX or MAE by BASF and the vinyl acetate/crotonic acid copolymers and the vinyl acetate/crotonic acid copolymers grafted by polyethylene glycol sold under the name Aristoflex® A by BASF.

The amphoteric fixing polymers which can be used for the present invention are chosen in particular from polymers comprising B and C units distributed randomly in the polymer chain, where B denotes a unit deriving from a monomer comprising at least one basic nitrogen atom and C denotes a unit deriving from a monomer comprising one or more carboxylic acid or sulphonic acid groups. The amphoteric fixing polymers can also comprise zwitterionic units of carboxybetaine or sulphobetaine type. They can also be polymers with a cationic main chain comprising primary, secondary, tertiary or quaternary amine groups, among which at least one carries, via a hydrocarbonaceous radical, a carboxylic acid or sulphonic acid group. The amphoteric fixing polymers can also have an anionic chain derived from α,β-unsaturated dicarboxylic acids, one of the carboxyl groups of which has been reacted with a polyamine comprising one or more primary or secondary amine groups.

The amphoteric fixing polymers corresponding to the definition given above are chosen in particular from the following polymers:

(1) Polymers resulting from the copolymerization of a vinyl monomer carrying a carboxylic acid group, such as acrylic acid, methacrylic acid, maleic acid or α-chloroacrylic acid, and of a vinyl monomer comprising at least one basic functional group, such as dialkylaminoalkyl methacrylate and acrylate or dialkylaminoalkyl(meth)acrylamides. Such compounds are disclosed, for example, in U.S. Pat. No. 3,836,537.

(2) Polymers comprising units derived:
  (a) from at least one monomer chosen from N-alkylated acrylamides or methacrylamides,
  (b) from at least one comonomer comprising one or more carboxylic acid functional groups, and
  (c) from at least one basic comonomer, such as esters comprising primary, secondary, tertiary or quaternary amine constituents of acrylic acid and of methacrylic acid and the quaternization product of dimethylaminoethyl methacrylate with dimethyl or diethyl sulphate.

The preferred N-alkylated acrylamides or methacrylamides (a) are those carrying $C_{2-12}$ alkyl radicals, such as N-ethylacrylamide, N-tert-butylacrylamide, N-tert-octylacrylamide, N-octylacrylamide, N-decylacrylamide, N-dodecylacrylamide and the corresponding methacrylamides.

The comonomers comprising a carboxylic acid group (b) are more particularly chosen from acrylic, methacrylic, crotonic, itaconic, maleic or fumaric acids and from the $C_{1-4}$ monoalkyl esters of maleic or fumaric acids or anhydrides.

The preferred basic comonomers (c) are aminoethyl methacrylate, butylaminoethyl methacrylate, N,N'-dimethylaminoethyl methacrylate and N-tert-butyl-aminoethyl methacrylate.

Use is made in particular of the copolymers for which the CFTA name (4th Ed., 1991) is "octylacrylamide/acrylates/butylaminoethyl methacrylate copolymer, such as the products sold under the name Amphomer® or Lovocryl® 47 by National Starch.

(3) Crosslinked and alkylated polyaminoamides partially or completely derived from polyaminoamides of general formula:

—[C(=O)—R₄—C(=O)-Z-]-    (II)

in which $R_4$ represents a divalent radical derived from a saturated dicarboxylic acid, from an aliphatic mono- or dicarboxylic acid comprising an ethylenic double bond, from a $C_{1-6}$ alkyl ester of these acids, or from a radical deriving from the addition of any one of the said acids to a bisprimary or bissecondary amine, and Z denotes a radical of a bisprimary, mono- or bissecondary polyalkylenepolyamine and preferably represents:

a) in the proportions of 60 to 100 mol %, the radical $$—NH—(CH_2)_x—NH]_p— \quad (III)$$

where x=2 and p=2 or 3, or else x=3 and p=2 this radical deriving from diethylenetriamine, triethylenetetraamine or dipropylenetriamine;

b) in the proportions of 0 to 40 mol %, the radical of formula (III) in which x=2 and p=1, derived from ethylenediamine, or the radical

derived from piperazine;

c) in the proportions of 0 to 20 mol %, the radical —NH—$(CH_2)_6$—NH— derived from hexamethylenediamine, these polyaminoamines being crosslinked by addition of 0.025 to 0.35 mol per mole of amine group of a bifunctional crosslinking agent chosen from epihalohydrins, diepoxides, dianhydrides or diunsaturated compounds and being alkylated with acrylic acid, chloroacetic acid or an alkanesultone.

The saturated carboxylic acids are preferably chosen from acids having 6 to 10 carbon atoms, such as adipic acid, 2,2,4-trimethyladipic and 2,4,4-trimethyladipic acid, terephthalic acid or acids comprising an ethylenic double bond, such as, for example, acrylic, methacrylic or itaconic acids.

The alkanesultones used in the alkylation are preferably propanesultone or butanesultone.

The salts of the alkylating agents are preferably the sodium or potassium salts.

(4) Polymers comprising zwitterionic units of formula:

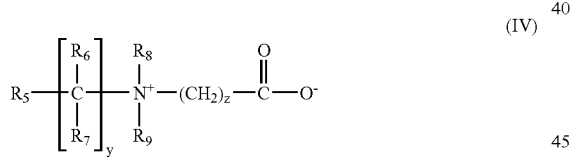

in which $R_5$ denotes a polymerizable unsaturated group, such as an acrylate, methacrylate, acrylamide or methacrylamide group, y and z each represent an integer from 1 to 3, $R_6$ and $R_7$ each independently represent a hydrogen atom or a methyl, ethyl or propyl group, and $R_8$ and $R_9$ each independently represent a hydrogen atom or an alkyl radical, the total number of carbon atoms in $R_8$ and $R_9$ not exceeding 10.

The polymers comprising such units of formula (IV) can additionally comprise units derived from nonzwitterionic monomers, such as dimethyl- or diethylaminoethyl-acrylate or methacrylate, alkyl acrylates or methacrylates, acrylamides or methacrylamides, or vinyl acetate.

Mention may be made, by way of example, of the methyl methacrylate/dimethylcarboxymethylammonioethyl methacrylate copolymer, such as the product sold under the name Diaformer® Z301 by Sandoz.

(5) Polymers derived from chitosan comprising monomer units corresponding to the following formulae:

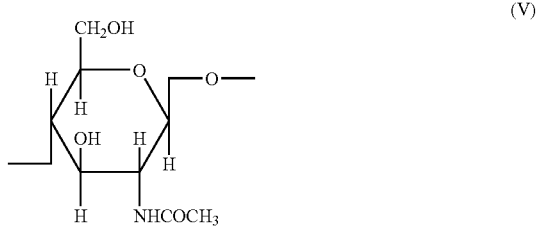

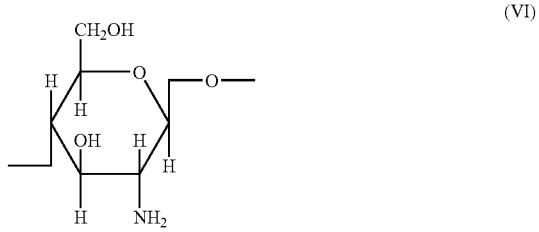

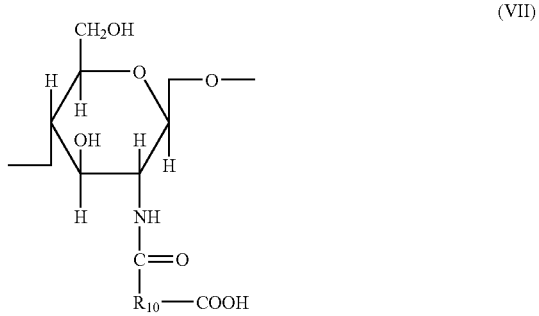

the unit of formula (V) being present in proportions of between 0 and 30%, the unit of formula (VI) in proportions of between 5 and 50% and the unit of formula (VII) in proportions of between 30 and 90%, it being understood that, in this unit (VII), $R_{10}$ represents a radical of formula:

in which:

if q=0, then $R_{11}$, $R_{12}$ and $R_{13}$, which are identical or different, each represent a hydrogen atom, a methyl, hydroxyl, acetoxy or amino group, a monoalkylamine or dialkylamine group optionally interrupted by one or more nitrogen atoms and/or optionally substituted by one or more amine, hydroxyl, carboxyl, alkylthio or sulpho groups, or an alkylthio group in which the alkyl group carries an amino residue, at least one of the $R_{11}$, $R_{12}$ and $R_{13}$ radicals being, in this case, a hydrogen atom; or if q=1, then $R_{11}$, $R_{12}$ and $R_{13}$ each represent a hydrogen atom, and the salts formed by these compounds with bases or acids.

(6) Polymers obtained by N-carboxyalkylation of chitosan, such as the N-(carboxymethyl)chitosan or the N-(carboxybutyl)chitosan sold under the name Evalsan® by Jan Dekker.

(7) Polymers corresponding to the general formula (IX)

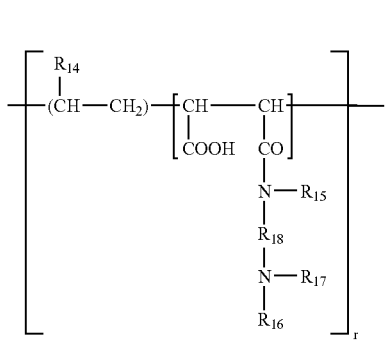

which are disclosed in particular in Patent FR 1 400 366, in which formula $R_{14}$ represents a hydrogen atom or a $CH_3O$, $CH_3CH_2O$ or phenyl radical, $R_{15}$ denotes a hydrogen atom or a lower alkyl radical, such as methyl or ethyl, $R_{16}$ denotes a hydrogen atom or a lower alkyl radical, such as methyl, or ethyl, and $R_{17}$ denotes a lower alkyl radical, such as methyl or ethyl, or a radical corresponding to the formula:

$-R_{18}-N(R_{16})_2$, $R_{18}$ representing a $-CH_2-CH_2-$, $CH_2-CH_2-CH_2-$ or $-CH_2-CH(CH_3)-$ group and $R_{16}$ having the meanings mentioned above, and the higher homologues of these radicals comprising up to 6 carbon atoms.

(8) Amphoteric polymers of the -D-X-D-X- type chosen from:

(a) polymers obtained by reaction of chloroacetic acid or sodium chloroacetate with compounds comprising at least one unit of formula:

-D-X-D-X-D-  (X)

where D denotes a radical

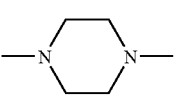

and X denotes the symbol E or E', E or E', which are identical or different, denoting a bivalent radical which is a straight- or branched-chain alkylene radical comprising up to 7 carbon atoms in the main chain, which chain is unsubstituted or substituted by hydroxyl groups and can additionally comprise oxygen, nitrogen or sulphur atoms or 1 to 3 aromatic and/or heterocyclic rings, the oxygen, nitrogen and sulphur atoms being present in the form of ether, thioether, sulphoxide, sulphone, sulphonium, alkylamine or alkenylamine groups or hydroxyl, benzylamine, amine oxide, quaternary ammonium, amide, imide, alcohol, ester and/or urethane groups, (b) polymers of formula:

-D-X'-D-X'-  (X')

where D denotes a radical

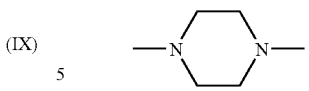

and X' denotes the symbol E or E' and at least once E', E having the meaning indicated above and E' being a bivalent radical which is a straight- or branched-chain alkylene radical having up to 7 carbon atoms in the main chain, which chain is substituted or unsubstituted by one or more hydroxyl radicals and which comprises one or more nitrogen atoms, the nitrogen atom being substituted by an alkyl chain optionally interrupted by an oxygen atom and necessarily comprising one or more carboxyl functional groups or one or more hydroxyl functional groups and betainized by reaction with chloroacetic acid or sodium chloroacetate.

(9) $(C_{1-5})$alkyl vinyl ether/maleic anhydride copolymers partially modified by semiamidation with an N,N-dialkylaminoalkylamine, such as N,N-dimethylaminopropylamine, or by semiesterification with an N,N-dialkanolamine. These copolymers can also comprise other vinyl comonomers, such as vinylcaprolactam.

The preferred amphoteric fixing polymers according to the invention are those of the abovedescribed family (3), such as those with the CTFA name "octylacrylamide/acrylates/butylaminoethyl methacrylate copolymer". Mention may be made, by way of examples, of the products sold under the names Amphomer®, Amphomer® LV 71 or Lovocryl® 47 by National Starch.

Other preferred amphoteric fixing polymers are those of family (4), such as, for example, copolymers of methyl methacrylate and of dimethylcarboxymethylammonioethyl methacrylate, sold, for example, under the name Diaformer® Z301 by Sandoz.

The anionic or amphoteric fixing polymers can, if necessary, be partially or completely neutralized. The neutralizing agents are, for example, sodium hydroxide, potassium hydroxide, 2-amino-methylpropanol, monoethanolamine, triethanolamine or triisopropanolamine, or inorganic or organic acids, such as hydrochloric acid or citric acid.

The nonionic fixing polymers which can be used according to the present invention are chosen, for example, from:
  vinylpyrrolidone homopolymers,
  copolymers of vinylpyrrolidone and of vinyl acetate,
  polyalkyloxazolines, such as the polyethyloxazolines provided by Dow Chemical under the names Peox® 50 000, Peox® 200 000 and Peox® 500 000,
  vinyl acetate homopolymers, such as the product provided under the name of Appretan® EM by Hoechst or the product provided under the name Rhodopas® A 012 by Rhône-Poulenc,
  copolymers of vinyl acetate and of acrylic esters, such as the product provided under the name Rhodopas® AD 310 by Rhône-Poulenc,
  copolymers of vinyl acetate and of ethylene, such as the product provided under the name of Appretan® TV by Hoechst,
  copolymers of vinyl acetate and of maleic ester, for example of dibutyl maleate, such as the product provided under the name of Appretan® MB Extra by Hoechst,
  copolymers of polyethylene and of maleic anhydride,
  alkyl acrylate homopolymers and alkyl methacrylate homopolymers, such as the product provided under the name Micropearl® RQ 750 by Matsumoto or the product provided under the name Luhydran® A 848 S by BASF, acrylic ester copolymers, such as, for example, copolymers of alkyl acrylates and of alkyl methacrylates, such as the products provided by the company Rohm & Haas under the names Primal AC-261 K and Eudragit NE 30 D, by BASF under the names Acronal® 601 or Luhydran® LR 8833 or 8845, and by Hoechst under the names Appretan® N 9213 or N9212, copolymers of acrylonitrile and of a nonionic monomer chosen, for example, from butadiene and alkyl (meth) acrylates; mention may be made of the products provided under the names Nipol® LX531B by Nippon Zeon or those provided under the name CJ 0610 B by Rohm & Haas, polyurethanes, such as the products provided under the names Acrysol® RM 1020 or Acrysol® RM 2020 by Rohm & Haas or the products Uraflex® XP401 UZ or Uraflex® XP and 402 UZ by DSM Resins, copolymers of alkyl acrylate and of urethane, such as the product 8538-33 sold by National Starch, polyamides, such as the product Estapor® LO 11 provided by Rhône-Poulenc, chemically modified or unmodified nonionic guar gums.

The unmodified nonionic guar gums are, for example, the products sold under the name Vidogum® GH 175 by Unipectine and under the name Jaguar® C by Meyhall. The modified nonionic guar gums which can be used according to the invention are preferably modified by $C_{1-6}$ hydroxyalkyl groups. Mention may be made, by way of examples, of the hydroxymethyl, hydroxyethyl, hydroxypropyl and hydroxybutyl groups.

These guar gums are well known in the art and can, for example, be prepared by reaction of the corresponding alkene oxides, such as, for example, propylene oxide, with guar gum, so as to obtain a guar gum modified by hydroxypropyl groups.

Such nonionic guar gums optionally modified by hydroxyalkyl groups are, for example, sold under the trade names Jaguar® HP8, Jaguar® HP60, Jaguar® HP120, Jaguar® DC293 and Jaguar® HP105 by Meyhall or under the name Galactasol® 4H4FD2 by Aqualon.

According to the invention, use may also be made, as fixing polymers, of film-forming polymers of grafted silicone type comprising a polysiloxane part and a part composed of a non-silicone organic chain, one of the two parts constituting the main chain of the polymer and the other being grafted onto the said main chain.

These polymers are, for example, disclosed in Patent Applications EP-A-0 412 704, EP-A-0 412 707, EP-A-0 640 105 and WO 95/00578, EP-A-0 582 152 and WO 93/23009 and U.S. Pat. Nos. 4,693,935, 4,728,571 and 4,972,037.

These polymers are preferably anionic or nonionic polymers.

Such polymers are, for example, the copolymers which can be obtained by radical polymerization from the mixture of monomers formed a) of 50 to 90% by weight of tert-butyl acrylate, b) of 0 to 40% by weight of acrylic acid, c) of 5 to 40% by weight of a silicone macromer of formula

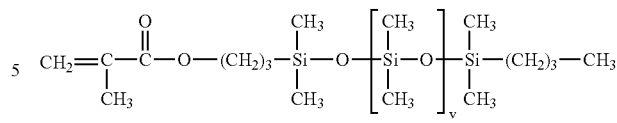

with v being a number ranging from 5 to 700, the percentages by weight being calculated with respect to the total weight of the monomers.

Other examples of grafted silicone polymers are in particular polydimethylsiloxanes (PDMS) on which are grafted, via a connecting link of thiopropylene type, mixed polymer units of the poly((meth)acrylic acid) type and of the poly (alkyl(meth)acrylate) type and polydimethylsiloxanes (PDMS) on which are grafted, via a connecting link of thiopropylene type, polymer units of the poly(isobutyl (meth)acrylate) type.

Use may also be made, as film-forming fixing polymers, of functionalized or non-functionalized and silicone or non-silicone polyurethanes.

The polyurethanes particularly targeted by the present invention are those disclosed in Patents EP 0 751 162, EP 0 637 600, FR 2 743 297 and EP 0 648 485 of the Applicant Company and Patent EP 0 656 021 or WO 94/03510 of BASF and EP 0 619 111 of National Starch.

The film-forming fixing polymers described above certainly have a satisfactory fixing power which makes possible good form retention of the hairstyle over time but they do not exhibit a sufficient thermoplastic nature. to allow thermal remodelling of the hairstyle. As indicated in the introduction, only the joint use of one or more conventional fixing polymers and of at least one crystalline hot-melt polymer described in more detail below makes it possible to obtain styling compositions which combine a good fixing power and excellent thermoplastic properties.

The amount of crystalline hot-melt polymer necessary to produce the desired effect, that is to say a sufficient thermoplasticity to allow hot remodelling of the hairstyle, depends, inter alia, on the chemical nature of the two types of polymers, on the molar masses of these polymers and on the desired fixing power and can vary within wide limits.

Generally, the ratio by weight of the total amount of crystalline hot-melt polymer to the total amount of film-forming fixing polymer is between 1/10 000 and 3/1 and preferably between 1/200 and 3/5.

The crystalline hot-melt polymers which can be used according to the present invention are preferably crystalline copolymers comprising i) from 85 to 98% by weight of hydrophobic units and ii) from 2 to 15% by weight of hydrophilic units.

The hydrophobic units are derived from α,β-ethylenic monomers with a $C_{12-50}$, preferably $C_{14-24}$, n-alkyl side chain which form crystalline homopolymers known in the literature as side chain crystalline polymers. They are in particular $C_{12-50}$ and preferably $C_{14-24}$ n-alkyl acrylates and methacrylates.

The hydrophilic units are preferably derived from α,β-unsaturated $C_{3-6}$ monocarboxylic acids, such as acrylic acid, methacrylic acid or crotonic acid, from unsaturated $C_{4-6}$ dicarboxylic acids, such as maleic acid and itaconic acid, or from the esters and amides comprising a $C_{1-4}$ alkyl chain of these monocarboxylic or dicarboxylic acids, such as $C_{1-4}$ alkyl (meth)acrylates and N—($C_{1-4}$ alkyl)-(meth)acrylamides.

The synthesis of these polymers is disclosed in particular in International Patent Application WO 98/25710.

Use may also be made, as hydrophilic unit, of hydroxyethyl methacrylate or vinylpyrrolidone.

The carboxylic acid groups of the hydrophilic units are preferably partially or completely neutralized by a base chosen, for example, from sodium hydroxide, potassium hydroxide, 2-amino-2-methylpropanol, monoethanolamine, triethanolamine or triisopropanolamine.

The crystalline hot-melt polymers which can be used in the present invention are furthermore characterized by a relatively low crystalline melting point, that is to say between 30 and 80° C.

The crystalline melting point of the polymers which can be used in the present invention is measured by differential scanning calorimetry.

This thermal analysis method makes it possible to demonstrate and to measure the crystallinity of a polymer. The enthalpy of fusion of a polymer is the amount of energy necessary to convert a partially or completely crystalline sample into a completely amorphous sample. The thermogram $\Delta Cp=f(T)$, in which $\Delta Cp$ represents the difference in heat capacity of the sample with respect to a reference sample which does not undergo any thermal transition in the range studied, thus exhibits an endothermic signal, the area of which is proportional to the enthalpy of fusion of the sample. Only the crystalline regions give rise to the melting phenomenon.

The melting point of the crystalline polymers which can be used in the present invention is measured rising a differential scanning calorimetry (DSC) device, model M2920CE-5010, sold by TA Instruments. The sample is heated, at a rate of 10° C./minute, from −20° C. to +150° C. and the difference in heat capacity between the sample and the control is recorded as a function of the temperature.

The term "crystalline melting point" ($T_m$) is used to denote the temperature corresponding to the tip of the endothermic melting peak of the crystalline regions which is thus obtained.

Mention may be made, by way of example of crystalline polymers with a low melting point, such as those described above, of a random copolymer sold under the name Structure® O by National Starch. It is a copolymer composed of 10% by weight of units derived from acrylic acid and of 90% by weight of units derived from n-octadecyl methacrylate. This copolymer has a crystalline melting point, measured by differential scanning calorimetry, of 46° C.

The styling compositions of the present invention, simultaneously comprising at least one film-forming fixing polymer and at least one crystalline hot-melt polymer, are liquid compositions and can be applied to the hair, for example, using means commonly used in the field of styling, such as an aerosol system or a sprayer.

The liquid phase of these systems comprises the fixing polymer or polymers in the dissolved or dispersed state and the crystalline hot-melt polymer or polymers in the dissolved state in a physiologically acceptable solvent.

Mention may be made, by way of examples of a physiological acceptable solvent, of water, lower $C_{1-4}$ alcohols, such as ethanol or isopropanol, acetone, methyl ethyl ketone, ethyl acetate, methyl acetate, butyl acetate, diethoxyethane, dimethoxyethane, $C_{6-10}$ alkanes or mixtures of these compounds.

The total concentration of polymers of this solution or dispersion, that is to say the concentration of film-forming fixing polymer and of crystalline hot-melt polymer, is preferably between 1 and 20% by weight with respect to the final styling composition.

The styling compositions of the present invention can additionally comprise various additives or adjuvants commonly used in the hair field, such as thickeners, anionic, nonionic, cationic or amphoteric surface-active agents, fragrances, preservatives, sunscreen agents, proteins, vitamins, provitamins, anionic, nonionic, cationic or amphoteric nonfixing polymers, mineral, vegetable or synthetic oils, ceramides, pseudoceramides, volatile or nonvolatile, linear or cyclic, modified or unmodified silicones, and any other additive conventionally used in compositions intended to be applied to the hair.

EXAMPLE

The following three compositions A, B and C are prepared:

| Composition | A | B | C |
|---|---|---|---|
| Crystalline polymer with aliphatic grafts, "Structure O" sold by National Starch | 4% | — | 1% |
| Mexomere PW (fixing polymer from Chimex) | — | 4% | 3% |
| 2-Amino-2-methyl-1-propanol | 0.5% | 0.5% | 0.5% |
| Absolute ethanol | 27% | 27% | 27% |
| Pentane | 33.5% | 33.5% | 33.5% |
| Dimethyl ether | 35% | 35% | 35% |

3 g of each of the above compositions A, B and C are applied, using an aerosol device, to a lock of hair (2.5 g of chestnut European hair with a length of approximately 20 cm).

After drying at ambient temperature, the locks of hair are disentangled using a comb and then heated on a flat support for 5 seconds using a hairdryer placed at a distance of 10 cm. The temperature reached at the surface of the hair during the heating is approximately 80° C. The locks are subsequently left at ambient temperature for 5 seconds.

The lock treated with solution A, which comprises the crystalline hot-melt polymer alone, certainly retains the flat shape imposed during heating but its cohesion between the hairs is completely unsatisfactory because of the extreme friability of the crystalline hot-melt polymer.

The lock treated with solution B, which comprises only the fixing polymer, remains completely soft and without any cohesion.

The lock treated with solution C according to the present invention, which comprises the combination of a fixing polymer and of a crystalline hot-melt polymer, retains the flat shape imposed during the heating stage and is distinguished by very good cohesion between the keratinous fibres. This lock can be remodelled (disentangling+heating with a hairdryer+cooling) approximately ten times without fresh product being introduced.

In conclusion, only the combination of the fixing polymer and of the crystalline hot-melt polymer makes possible remodelling of the lock of hair.

What is claimed is:

1. A styling composition comprising, in a physiologically acceptable medium,
   (a) at least one film-forming fixing polymer, and
   (b) at least one crystalline hot-melt polymer which is soluble in said medium and has a crystalline melting temperature, measured by differential scanning calorimetry, of between 30° C. and 80° C. and wherein said crystalline hot-melt polymer is a copolymer comprising approximately 10% by weight of units derived from acrylic acid and approximately 90% by weight of units derived from octadecyl methacrylate.

2. The styling composition according to claim 1, wherein said crystalline hot-melt polymer comprises i) at least one hydrophobic unit derived from α,β-ethylenic monomers with a $C_{12-50}$ n-alkyl side chain which forms crystalline homopolymers, said hydrophobic unit being present in an amount of 85% to 98% by weight, and ii) at least one hydrophilic unit derived from α,β-unsaturated $C_{3-6}$ monocarboxylic acids, unsaturated $C_{4-6}$ dicarboxylic acids, esters and amides comprising a $C_{1-4}$ alkyl chain of said monocarboxylic or dicarboxylic acids, hydroxyethyl methacrylate or vinylpyrrolidone, said hydrophilic unit being present in an amount of 2% to 15% by weight.

3. The styling composition of claim 1, wherein said film-forming fixing polymer is selected from the group consisting of anionic, cationic, amphoteric and nonionic film-forming fixing polymers.

4. The styling composition of claim 1, wherein the ratio by weight of said hot-melt polymer (b) to the fixing polymer (a) is between 1/10,000 and 3/1.

5. The styling composition of claim 1, wherein the total amount of the fixing polymer (a) and the hot-melt polymer (b) is between 1% and 20% by weight with respect to the final styling composition.

6. The styling composition of claim 1, wherein said physiologically acceptable liquid medium comprises a solvent selected from the group consisting of water, a lower $C_{1-4}$ alcohol, acetone, methyl ethyl ketone, ethyl acetate, methyl acetate, butyl acetate, diethoxyethane, dimethoxyethane, a $C_{6-10}$ alkane, and a mixture thereof.

7. A process for remodelling hair comprising (1) applying the styling composition of claim 1 to the hair, (2) giving the hair a desired shape by heating the hair to a temperature close to or greater than the crystalline melting temperature of the crystalline hot-melt polymer, and (3) allowing the hair to cool to a temperature below said crystalline melting temperature of said crystalline hot-melt polymer.

8. The styling composition of claim 2, wherein the hydrophobic unit is derived from an α,β-ethylenic monomer with a $C_{14-24}$ n-alkyl side chain.

9. The styling composition of claim 1, wherein the ratio by weight of the hot-melt polymer (b) to the fixing polymer (a) is between 1/200 and 3/5.

10. The styling composition of claim 1, wherein the physiologically acceptable liquid medium is ethanol or isopropanol.

11. The process of claim 7, and further comprising repeating steps (2) and (3).

12. The styling composition according to claim 2, wherein the at least one hydrophobic unit derived from α,β-ethylenic monomers has a $C_{14-24}$ n-alkyl side chain which forms crystalline homopolymers.

13. The styling composition of claim 12, wherein the ratio by weight of the hot-melt polymer (b) to the fixing polymer (a) is between 1/200 and 3/5.

* * * * *